United States Patent
Shin (12)

(10) Patent No.: US 12,082,923 B2
(45) Date of Patent: Sep. 10, 2024

(54) POSTURE MONITORING DEVICE EMPLOYING ELASTIC RESISTANCE ELEMENT, AND METHOD AND SYSTEM FOR MONITORING POSTURE BY USING SAME

(71) Applicant: Sung Joon Shin, Incheon (KR)

(72) Inventor: Sung Joon Shin, Incheon (KR)

( * ) Notice: Subject to any disclaimer, the term of this patent is extended or adjusted under 35 U.S.C. 154(b) by 556 days.

(21) Appl. No.: 16/641,631

(22) PCT Filed: Aug. 31, 2018

(86) PCT No.: PCT/KR2018/010162
§ 371 (c)(1),
(2) Date: Feb. 24, 2020

(87) PCT Pub. No.: WO2019/045526
PCT Pub. Date: Mar. 7, 2019

(65) Prior Publication Data
US 2020/0297248 A1   Sep. 24, 2020

(30) Foreign Application Priority Data

Aug. 31, 2017 (KR) .................. 10-2017-0110700
Aug. 31, 2018 (KR) .................. 10-2018-0103472

(51) Int. Cl.
*A61B 5/11* (2006.01)
*A61B 5/00* (2006.01)

(52) U.S. Cl.
CPC .......... *A61B 5/1116* (2013.01); *A61B 5/4561* (2013.01); *A61B 5/6802* (2013.01); *A61B 5/6823* (2013.01); *A61B 5/746* (2013.01)

(58) Field of Classification Search
CPC ... A61B 5/1116; A61B 5/4561; A61B 5/6802; A61B 5/6823; A61B 5/746; A61B 2010/00339
See application file for complete search history.

(56) References Cited

U.S. PATENT DOCUMENTS 5,749,838 A   5/1998  Kline
6,168,569 B1  1/2001  McEwen et al.
(Continued)

FOREIGN PATENT DOCUMENTS

CN   105266817 A   1/2016
CN   105662682 A   6/2016
(Continued)

OTHER PUBLICATIONS

International Search Report, dated Dec. 12, 2018, for International Patent Application No. PCT/KR2018/010162, with English Translation.
(Continued)

*Primary Examiner* — Patrick Fernandes
(74) *Attorney, Agent, or Firm* — INVENSTONE PATENT, LLC

(57) ABSTRACT

Disclosed herein is to a posture monitoring device for measuring and correcting a user's posture by utilizing a resistance element which is elastic and has a resistance which is changed according to mechanical strain. The posture monitoring device includes a first elastic resistance element and a second elastic resistance element which are configured to be attached onto skins of the first part and the second part or inserted into the skins, disposed to measure the degree of stretching of the skin of the first part in a longitudinal direction of the spinal column, and made of a conductive material to have elasticity, a power supply device for applying a current or a voltage to the first elastic resistance element, and the second elastic resistance element, and a communication module for transmitting data output from the first elastic resistance element and the second elastic resistance element to a controller.

12 Claims, 5 Drawing Sheets

(56) References Cited

U.S. PATENT DOCUMENTS

| | | | |
|---|---|---|---|
| 2010/0036287 A1* | 2/2010 | Weber | G01L 1/242 |
| | | | 600/595 |
| 2013/0201021 A1 | 8/2013 | Limonadi | |
| 2015/0374266 A1 | 12/2015 | Cohen et al. | |
| 2017/0103636 A1 | 4/2017 | Tu | |

FOREIGN PATENT DOCUMENTS

| | | |
|---|---|---|
| DE | 202005015889 U1 | 1/2006 |
| JP | 2008-536636 | 9/2008 |
| JP | 2010-42235 A | 2/2010 |
| JP | 2010-508133 A1 | 3/2010 |
| JP | 2015-134149 A2 | 7/2015 |
| KR | 20090009645 | 1/2009 |
| KR | 20120004579 A | 1/2012 |
| KR | 20130022542 | 3/2013 |
| KR | 20140004320 A | 1/2014 |
| KR | 20160048617 A | 5/2016 |
| KR | 20170000353 A | 1/2017 |
| KR | 20170058828 | 5/2017 |

OTHER PUBLICATIONS

Written Opinion, dated Dec. 12, 2018, for International Patent Application No. PCT/KR2018/010162. No Translation available.

* cited by examiner

POSTURE MONITORING DEVICE EMPLOYING ELASTIC RESISTANCE ELEMENT, AND METHOD AND SYSTEM FOR MONITORING POSTURE BY USING SAME

TECHNICAL FIELD

The present invention relates to a posture monitoring device and a method and a system for monitoring a posture using the same, and more particularly, to a posture monitoring device for measuring and correcting a user's posture by utilizing a resistance element which is elastic and has a resistance which is changed according to mechanical strain, and a method and a system for monitoring a posture using the same.

BACKGROUND ART

With the development of computer science and the development of the economy, as the working and academic environment is changed, the sedentary time rather than dynamic physical activity has been rapidly increased. In such an environment, when an incorrect posture is maintained for a long time, fatigue is easily felt, and particularly, backache and cervical pain are easily caused.

Pain in the lumbar and cervical spinal column is a major spinal disease that 80% or higher of the total population experiences by various causes and is caused by an incorrect posture as well as the cause of spinal injury.

Until the curvature of the spinal column is severely worsened, the curvature of the spinal column may be sufficiently alleviated and improved only by treatment with correct posture and correct habits, rather than recovery through direct treatment. Recently, the development of a posture monitoring system capable of measuring and correcting the posture has been actively performed.

For example, there are proposed a system for monitoring a sitting posture in real time by attaching a pressure sensor to a chair to sense the pressure applied to the chair by a body (see Prior Art 1), a system for monitoring a posture based on a captured image by attaching a camera to a display device such as a monitor to capture a user's posture (see Prior Art 2), and a system for monitoring a posture by wearing clothes with an EMG sensor, an inertial sensor, etc. and analyzing a signal sensed from various sensors (see Prior Art 3).

However, such a conventional system requires a separate sensing means such as a chair with a sensor, a photographing device such as a camera, and clothes equipped with a sensor to determine a user's posture. In the case of Prior Arts 1 and 2, there is a limitation that it may only be used under quite limited conditions in that it is possible to monitor the posture only when the user takes a sitting position at a specific position. In the case of Prior Art 3, there is an inconvenience to the user's activities in terms of attaching various sensors to the body, acquisition of measurement information or a processing algorithm is complicated, and it is difficult to accurately determine the user's posture in real time.

(Patent Document 1) 1. Korean Patent Publication No. 10-2016-0048617 (Title of the invention: Real-time sitting posture monitoring system using pressure sensor)

(Patent Document 2) 2. Korean Patent Publication No. 10-2014-0004320 (Title of the invention: Posture correction system through periodic monitoring)

(Patent Document 3) 3. Korean Patent Publication No. 10-2017-0000353 (Title of the invention: Apparatus for measuring bioelectric signal for correcting posture)

DISCLOSURE

Technical Problem

The present invention is derived to solve the problems above and directed to providing a posture measuring and correcting device including elastic resistance elements which are attached onto or inserted into the body of a user so that the resistance is sensitively changed according to mechanical strain depending on a user's posture, and a monitoring method and system utilizing the same.

Further, the present invention is directed to providing a posture monitoring device configured to be easily portable and be used in everyday life without spatial constraints as compared with a conventional posture monitoring device by using the posture monitoring device of the present invention by the user.

Further, the present invention is directed to providing a posture monitoring device, method, and system configured to check posture information in real time and correct the posture by interlocking a terminal such as a smart phone with a monitoring device provided in the body of the user.

Further, the present invention is directed to providing a posture monitoring device, method, and system capable of transmitting a signal to correct a posture to a user by utilizing an alarm function when the user maintains an improper posture for a predetermined time or higher.

The objects of the present invention are not limited to the aforementioned object, and other objects, which are not mentioned above, will be apparent to a person having ordinary skill in the art from the following description.

Technical Solution

One aspect of the present invention provides a posture monitoring device configured to monitor a posture by measuring the degree of stretching a first part and a second part of a dorsal part which are divided by the spinal column, the posture monitoring device including: a first elastic resistance element which is configured to be attached onto or inserted into the skin of the first part, disposed to measure the degree of stretching of the skin of the first part in a longitudinal direction of the spinal column, and made of a conductive material to have elasticity; a second elastic resistance element which is configured to be attached onto or inserted into the skin of the second part, disposed to measure the degree of stretching of the skin of the second part in a longitudinal direction of the spinal column, and made of a conductive material to have elasticity; a power supply device configured to apply a current or a voltage to the first elastic resistance element and the second elastic resistance element through electrodes formed on both ends of each of the first elastic resistance element and the second elastic resistance element; and a communication module configured to transmit data output from the first elastic resistance element and the second elastic resistance element to a controller so as to calculate information about mechanical strain occurring in the first elastic resistance element and the second elastic resistance element and information about curvatures of the body on the first part and the second part.

Further, according to another feature of the present invention, the output data may be data about at least one of resistance, current, and voltage of the first elastic resistance element and the second elastic resistance element.

Further, according to another feature of the present invention, the first elastic resistance element and the second elastic resistance element may contain conductive carbon particles and be disposed in the form of strings in the longitudinal direction of the spinal column.

Further, according to another feature of the present invention, a plurality of first elastic resistance elements and second elastic resistance elements may be provided, respectively, and the output data may be an average value of the data output from the plurality of first elastic resistance elements and an average value of the data output from the plurality of second elastic resistance elements.

Further, according to another feature of the present invention, the posture monitoring device may further include a first stimulating element which is attached onto the skin of the first part or inserted to be located into the skin and configured to apply stimulation to the skin or muscle of the first part; and a second stimulating element which is attached onto the skin of the second part or inserted to be located into the skin and configured to apply stimulation to the skin or muscle of the second part.

Further, according to another feature of the present invention, the posture monitoring device may further include a third elastic resistance element which is configured to be attached onto the skin or inserted into the skin, disposed to measure the degree of stretching of the skin of a third part which is distinguished from the first part and the second part in a direction perpendicular to the longitudinal direction of the spinal column, and made of a conductive material to have elasticity.

Further, according to another feature of the present invention, the posture monitoring device may further include a third stimulating element which is attached onto the skin of the third part or inserted to be located into the skin and configured to apply stimulation to the skin or muscle of the third part.

Further, according to another feature of the present invention, the posture monitoring device may further include a fourth elastic resistance element which is configured to be attached onto the skin or inserted into the skin, disposed to measure the degree of stretching of the skin of a fourth part which is distinguished from the first part and the second part in a direction parallel to the longitudinal direction of the spinal column, and made of a conductive material to have elasticity.

Further, according to another feature of the present invention, the posture monitoring device may further include a fourth stimulating element which is attached onto the skin of the fourth part or inserted to be located into the skin and configured to apply stimulation to the skin or muscle of the fourth part.

Another aspect of the present invention provides a posture monitoring method configured to monitor a posture by measuring the degree of stretching a first part and a second part of a dorsal part which are divided by the spinal column, the posture monitoring method including: receiving data of at least one of resistance, current, and voltage output from a first elastic resistance element and a second elastic resistance element, from a posture monitoring device including a first elastic resistance element which is configured to be attached onto the skin of the first part or inserted to be located into the skin, disposed to measure the degree of stretching of the skin of the first part in a longitudinal direction of the spinal column, and made of a conductive material to have elasticity, a second elastic resistance element which is configured to be attached onto the skin of the second part or inserted to be located into the skin, disposed to measure the degree of stretching of the skin of the second part in a longitudinal direction of the spinal column, and made of a conductive material to have elasticity, and a power supply device configured to apply a current or a voltage to the first elastic resistance element and the second elastic resistance element through electrodes formed on both ends of each of the first elastic resistance element and the second elastic resistance element; calculating information about mechanical strain occurring in the first elastic resistance element and the second elastic resistance element, based on the data; and measuring the degree of curvatures of the body in the first part and the second part based on the information about mechanical strain.

Further, according to another feature of the present invention, the posture monitoring method may further include determining whether the degree of curvatures of the body in the first part and the second part is a preset threshold or higher.

Further, according to another feature of the present invention, the posture monitoring device may further include a first stimulating element which is attached onto the skin of the first part or inserted to be located into the skin and configured to apply stimulation to the skin or muscle of the first part and a second stimulating element which is attached onto the skin of the second part or inserted to be located into the skin and configured to apply stimulation to the skin or muscle of the second part, and the posture monitoring method may further include transmitting a signal so that at least one of the first stimulating element and the second stimulating element applies stimulation to the skin or muscle, when the degree of curvature of the body in at least one of the first part and the second part is determined as the preset threshold or higher in the determining.

Further, according to another feature of the present invention, the posture monitoring method may further include transmitting an alarm signal to an external terminal, when the degree of curvature of the body in at least one of the first part and the second part is determined as the preset threshold or higher in the determining.

Yet another aspect of the present invention provides a posture monitoring system configured to monitor a posture by measuring the degree of stretching a first part and a second part of a dorsal part which are divided by the spinal column, the posture monitoring system including: a posture monitoring device including a first elastic resistance element which is configured to be attached onto or inserted into the skin of the first part, disposed to measure the degree of stretching of the skin of a first part in a longitudinal direction of the spinal column, and made of a conductive material to have elasticity, a second elastic resistance element which is configured to be attached onto or inserted into the skin of the second part, disposed to measure the degree of stretching of the skin of the second part in a longitudinal direction of the spinal column, and made of a conductive material to have elasticity, a power supply device configured to apply a current or a voltage to the first elastic resistance element and the second elastic resistance element through electrodes formed on both ends of each of the first elastic resistance element and the second elastic resistance element, and a communication module configured to transmit data output from the first elastic resistance element and the second elastic resistance element so as to calculate information about mechanical strain occurring in the first elastic resistance element and the second elastic resistance element and information about curvatures of the body on the first part and the second part; and a controller configured to receive data of at least one of resistance, current, and voltage output from the first elastic resistance element and the second elastic resistance element, from the posture monitoring device, calculate information about mechanical strain occurring in the first elastic resistance element and the second elastic resistance element, based on the data, and measure the degree of curvatures of the body in the first part and the second part based on the information about mechanical strain.

Advantageous Effects

According to the posture monitoring device, method, and system of the present invention, it is possible to provide a posture monitoring device, method, and system with efficiently improved ease of the use as compared with a conventional posture monitoring device requiring various sensors or equipment while efficiently measuring various postures of the user, by utilizing the elastic resistance elements which are attached onto or inserted into the body of a user so that the resistance is sensitively changed according to mechanical strain.

In particular, according to the posture monitoring device, method and system of the present invention, it is possible to be easily portable and be used in everyday life without spatial constraints.

Further, according to the posture monitoring device, method and system of the present invention, it is possible to utilize a measuring means which is suitable for measuring various postures of the user causing bending or twisting, and other various strains and is not strained even in repeated use, by utilizing a resistance element of which the shape is freely changed by an external force and then restored to an original state without a damage when the external force is released.

Further, according to the posture monitoring device, method and system of the present invention, it is possible to check posture information in real time by interlocking a terminal such as a smart phone with a monitoring device provided in the body of the user.

Further, according to the posture monitoring device, method, and system of the present invention, when the user maintains an improper posture for a predetermined time or higher, a signal to correct the posture is transmitted to the user, thereby preventing diseases such as discopathy (disc disease) of the spinal column or cyphosis and scoliosis.

Further, according to the posture monitoring device, method, and system of the present invention, by inducing patients having surgery due to a spinal lesion and required to maintain a correct posture for a certain period of time to maintain the correct posture, it is possible to prevent post-operative complications.

MODES OF THE INVENTION

Figure 1:
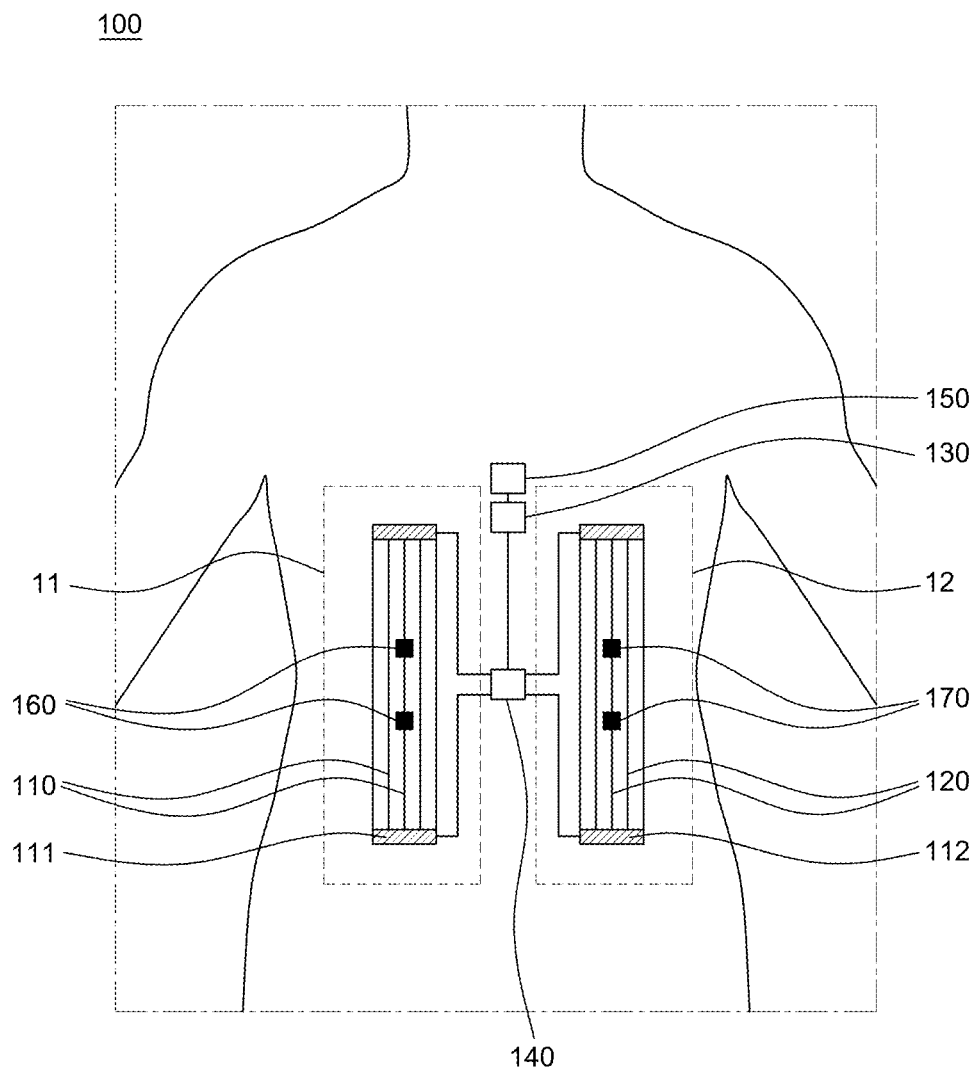
FIG. 1 is a configuration diagram schematically illustrating a posture monitoring device according to an exemplary embodiment of the present invention.

Advantages and features of the present invention, and methods for accomplishing the same will be more clearly understood from exemplary embodiments described in detail below with reference to the accompanying drawings. However, the present disclosure is not limited to the following exemplary embodiments but may be implemented in various different forms. The exemplary embodiments are provided only to make description of the present disclosure complete and to fully provide the scope of the present disclosure to a person having ordinary skill in the art to which the present disclosure pertains with the category of the invention, and the present disclosure will be defined by the appended claims.

When elements or layers are referred to as being "on" another element or layer, it may be directly on the other element or layer, or intervening elements or layers may be present.

Although the terms "first", "second", and the like are used for describing various components, these components are not confined by these terms. These terms are merely used for distinguishing one component from another component. Therefore, a first component to be mentioned below may be a second component in a technical concept of the present invention.

Throughout the whole specification, the same reference numerals denote the same elements.

Since the size and thickness of each component illustrated in the drawings are represented for convenience in explanation, the present disclosure is not necessarily limited to the illustrated size and thickness of each component.

The features of various exemplary embodiments of the present disclosure can be partially or entirely bonded to or combined with each other and can be interlocked and operated in technically various ways, and the exemplary embodiments can be carried out independently of or in association with each other.

Hereinafter, a posture monitoring device, and a method and a system for monitoring a posture using the same will be described in detail with reference to the accompanying drawings.

First, a posture monitoring device of the present invention will be described in detail with reference to FIGS. 1, 2A, and 2B.

Figure 2A:
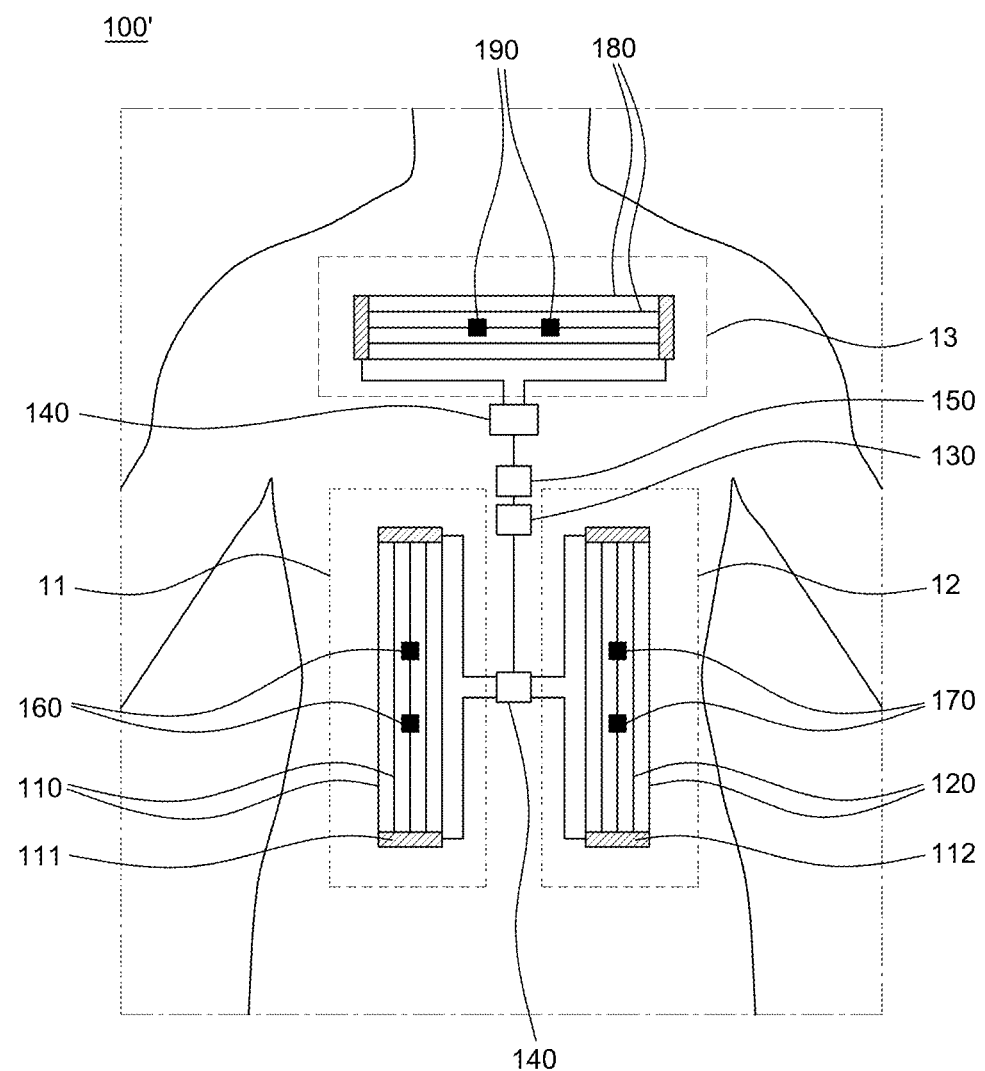
FIGS. 2A and 2B are configuration diagrams schematically illustrating a posture monitoring device according to another exemplary embodiment of the present invention.
Figure 2B:
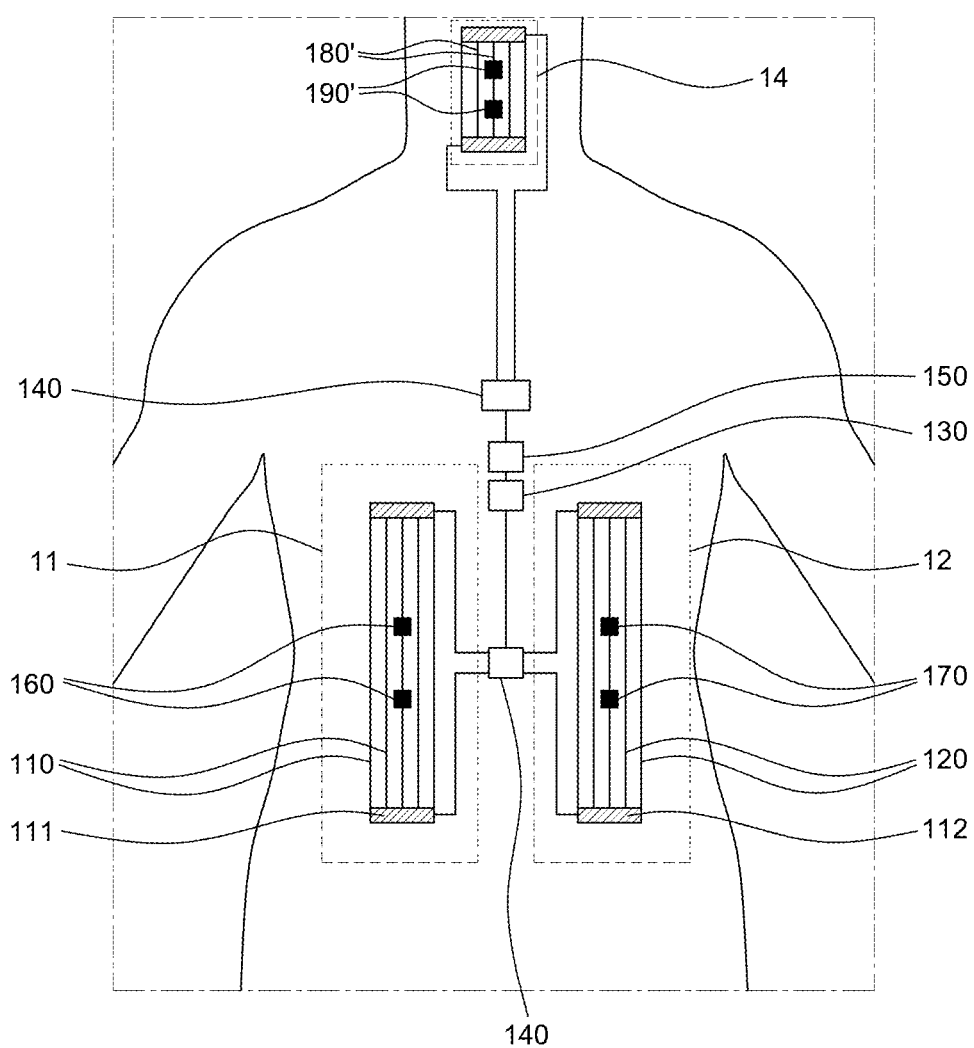

FIG. 1 is a configuration diagram schematically illustrating a posture monitoring device according to an exemplary embodiment of the present invention and FIGS. 2A and 2B are configuration diagrams schematically illustrating a posture monitoring device according to another exemplary embodiment of the present invention.

Referring to FIG. 1, a posture monitoring device 100 of the present invention includes a first elastic resistance element 110 and a second elastic resistance element 120 which are configured to be attached onto the skin or inserted into the skin, a power supply device 130 for applying a current or a voltage to the first elastic resistance element 110 and the second elastic resistance element 120, a resistance measuring device 140 for measuring variable resistances of the first elastic resistance element 110 and the second elastic resistance element 120, and a communication module 150 for transmitting data output from the resistance measuring device 140 to an external device.

The first elastic resistance element 110 and the second elastic resistance element 120 are elements which are configured to measure the degree of stretching of a first part 11 and a second part 12 on a dorsal part, which are divided by the spinal column of the body. The first elastic resistance element 110 and the second elastic resistance element 120 are made of conductive materials to have elasticity and have a characteristic in which the resistance is sensitively changed according to mechanical strain depending on a user's posture.

Here, the dorsal part means the neck, the back, the waist of the back of the spinal column, and for convenience of description, the exemplary embodiment illustrates that the elastic resistance elements 110 and 120 are disposed on the back part, but is not limited thereto.

In this case, as illustrated in FIG. 1, the first elastic resistance element 110 and the second elastic resistance element 120 are arranged in the form of strings in a longitudinal direction of the spinal column, and electrodes 111 and 112 of the first elastic resistance element 110 and the second elastic resistance element 120 may be formed at both ends. However, the forms of the elastic resistance elements 110 and 120 illustrated in FIG. 1 are illustrative, and for example, it should be noted that the resistance elements 110 and 120 may be variously modified in the form of wide strings.

At this time, the first elastic resistance element 110 and the second elastic resistance element 120 may be configured to be attached onto skins of the first part 11 and the second part 12 or to be inserted into the skins, respectively.

For example, the first elastic resistance element 110 and the second elastic resistance element 120 may be resistance elements manufactured in various structures in a film form and a three-dimensional form through a combination of a stretchable elastic material and conductive nanoparticles. The elastic material may be polydimethyl siloxane (PDMS), which is a kind of silicone rubber having elasticity and flexibility, and the conductive nanoparticles may be carbon particles. In addition, the conductive nanoparticles may be nanomaterials having high conductivity, such as carbon nanotubes, graphene, metal nanowires, and metal nanoparticles. At this time, it is preferable that the materials forming the first elastic resistance element 110 and the second elastic resistance element 120 are adopted as a material having a small change in specific resistance due to external influences (temperature, humidity, etc.).

Meanwhile, the first elastic resistance element 110 and the second elastic resistance element 120 may also be formed in the form in which an electronic ink (E-ink) containing conductive nanoparticles and manufactured to be applied to the skin is applied to the skin or inserted into the skin (e.g., tattoo). Such an E-ink may employ a configuration of conductive ink that is safe for the skin disclosed in Korean Patent Publication No. 10-2011-0133556.

When the E-ink is applied to the skin or inserted into the skin to form the first elastic resistance element 110 and the second elastic resistance element 120, the E-ink is preferably made of a material that can be combined with living tissue, is a soft and elastic material, and is harmless to the human body. In addition, when a current flowing in the first elastic resistance element 110 and the second elastic resistance element 120 may cause a direct effect (e.g., electric shock) on the tissue, it is preferable that an insulating layer is formed between the first elastic resistance element 110 and the second elastic resistance element 120 and the skin or subcutaneous tissue.

The insulating layer may also be formed to surround the first elastic resistance element 110 and the second elastic resistance element 120, or may also be formed in the form of a film in contact with the skin or subcutaneous tissue. In addition to the illustrated shapes, of course, the insulating layer may be formed to protect the skin or subcutaneous tissue in various ways. At this time, it is preferable that the insulating layer is formed of a material having the same or similar elasticity as or to that of the elastic resistance elements 110 and 120.

In addition, the first elastic resistance element 110 and the second elastic resistance element 120 may be applied in various forms (e.g., a film form, etc.) in which the resistance is sensitively changed according to mechanical strain, and of course, a technique known as a flexible tactile material capable of sensing changes in the body such as pressure and strain may be applied to the present invention.

The power supply device 130 applies a voltage or current to the first elastic resistance element 110 and the second elastic resistance element 120 by the electrodes 111 and 112.

When the voltage or current is applied to the first elastic resistance element 110 and the second elastic resistance element 120 by the power supply device 130, the resistance measuring device 140 may measure the current or voltage flowing in the first elastic resistance element 110 and the second elastic resistance element 120 to calculate the resistances of the first elastic resistance element 110 and the second elastic resistance element 120.

The displacement of the calculated resistances of the first elastic resistance element 110 and the second elastic resistance element 120 or the changed resistances is used for calculating information about mechanical strain occurring in the first elastic resistance element 110 and the second elastic resistance element 120 and information about the curvatures of the body in the first part 11 and the second part 12. This will be described below with reference to FIGS. 3 and 4.

The communication module 150 transmits data output from the resistance measuring device 140, that is, data about at least one of resistance, current, and voltage, to an external device.

The communication module 150 is preferably a Bluetooth module. However, the present invention is not limited thereto, and of course, the communication module 150 may be a near field communication module such as radio frequency identification (RFID), infrared data association (IrDA), ZigBee, and Wi-Fi Direct, and any known network may be used.

Meanwhile, a plurality of first elastic resistance elements 110 and second elastic resistance elements 120 may be provided. As illustrated in FIG. 1, the plurality of first elastic resistance elements 110 and second elastic resistance elements 120 configured in the form of strings in a longitudinal direction of the spinal column may be connected to each other and arranged in parallel.

In this case, the resistance measuring device 140 may calculate an average value of data output from the first elastic resistance elements 110 and the second elastic resistance elements 120 to provide the average value to the communication module 150. Each data output from the first elastic resistance elements 110 and the second elastic resistance elements 120 may also be provided to the communication module 150 without a separate operation.

Furthermore, the posture monitoring device 100 of the present invention further includes a first stimulating element 160 and a second stimulating element 170 which are attached onto the skins of the first part 11 and the second part 12 or inserted to be located inside the skins.

The first stimulating element 160 and the second stimulating element 170 are configured to apply stimulation to the skins or muscles of the first part 11 and the second part 12. For example, the first stimulating element 160 and the second stimulating element 170 may be elements configured to apply stimulation to the user's skin or muscle in the same manner as electrical muscle stimulation or transcutaneous electrical nerve stimulation. In this case, the stimulation applied by the first stimulating element 160 and the second stimulating element 170 may be an electrical stimulation signal, and in addition, may also be a vibration stimulation signal.

The first stimulating element 160 and the second stimulating element 170 may be configured to operate upon receiving a stimulation signal from the communication module 150, and the operation of the first stimulating element 160 and the second stimulating element 170 will be described below with reference to FIGS. 3 and 4.

As illustrated in FIG. 1, the first stimulating element 160 and the second stimulating element 170 are arranged in the form of a string together with the first elastic resistance element 110 and the second elastic resistance element 120 to be elongated in the longitudinal direction of the spinal column. Further, the first stimulating element 160 and the second stimulating element 170 may be disposed to be connected in parallel with the first elastic resistance element 110 and the second elastic resistance element 120, so as to share the first elastic resistance element 110 and the electrode 111 and share the second elastic resistance element 120 and the electrode 112, respectively.

However, the arrangement manner of the first stimulating element 160 and the second stimulating element 170 is not limited to the illustrated, and so long as the stimulation may be applied to the first part 11 and the second part 12, of course, the first stimulating element 160 and the second stimulating element 170 may be arranged in various structures.

Meanwhile, referring to FIG. 2A, a posture monitoring device 100' of the exemplary embodiment may further include a third elastic resistance element 180 in a third part 13 which is distinguished from the first part 11 and the second part 12. The third elastic resistance element 180 may be included in the posture monitoring device of the present invention in addition to the first elastic resistance element 110 and the second elastic resistance element 120, and is preferably disposed to monitor a posture of the shoulder portion of the user.

The third elastic resistance element 180 is also configured to be attached onto the skin or inserted into the skin like the first elastic resistance element 110 and the second elastic resistance element 120, and may be disposed to measure the degree of stretching of the skin of the third part 13. However, unlike the first elastic resistance element 110 and the second elastic resistance element 120, the third elastic resistance element 180 may be disposed to measure the degree of stretching of the skin in a direction perpendicular to the longitudinal direction of the spinal column.

The posture monitoring device 100' further includes the third elastic resistance element 180 in the third part 13 to have an advantage of more precisely monitoring various postures by measuring the stretching of the skins of the first part 11, the second part 12, and the third part 13.

Further, referring to FIG. 2B, a posture monitoring device 100" of the exemplary embodiment may further include a fourth elastic resistance element 180' in a fourth part 14 which is distinguished from the first part 11 and the second part 12. The fourth elastic resistance element 180' may be included in the posture monitoring device of the present invention in addition to the first elastic resistance element 110 and the second elastic resistance element 120, and is preferably disposed to monitor a posture of the neck portion of the user.

The fourth elastic resistance element 180' is also configured to be attached onto the skin or inserted into the skin like the first elastic resistance element 110 and the second elastic resistance element 120, and may be disposed to measure the degree of stretching of the skin of the fourth part 14. However, unlike the third elastic resistance element 180, the fourth elastic resistance element 180' may be disposed to measure the degree of stretching of the skin in a direction parallel to the longitudinal direction of the spinal column.

The posture monitoring device 100" further includes the fourth elastic resistance element 180' in the fourth part 14 to have an advantage of more precisely monitoring various postures by measuring the stretching of the skins of the first part 11, the second part 12, and the fourth part 14.

Meanwhile, in FIGS. 2A and 2B, although the first part 11, the second part 12, the third part 13, and the fourth part 14 are illustrated as being independent of each other, the third part 13 and the fourth part 14 may partially overlap with the first part 11 and the second part 12.

Since a driving principle of the third elastic resistance element 180 and the fourth elastic resistance element 180' is the same as that of the first elastic resistance element 110 and the second elastic resistance element 120, a duplicated description will be omitted.

In addition, the posture monitoring devices 100' and 100" of the present invention may further include a third stimulating element 190 or fourth stimulating element 190' configured to apply stimulation to the skin or muscle in the third part 13 or the fourth part 14 which is distinguished from the first part 11 and the second part 12. The third stimulating element 190 and the fourth stimulating element 190' may be included in the posture monitoring device of the present invention in addition to the first stimulating element 160 and the second stimulating element 170, and are preferably disposed to correct a posture of the shoulder or neck portion of the user.

Since a driving principle of the third stimulating element 190 and the fourth stimulating element 190' is the same as that of the first stimulating element 160 and the second stimulating element 170, a duplicated description will be omitted.

Meanwhile, as illustrated in FIGS. 2A and 2B, the third elastic resistance element 180 and the fourth elastic resistance element 180' may be performed independently of each other or may be performed by overlapping with each other. When performed by overlapping with each other, posture control of the shoulder and neck portions is also possible.

Hereinafter, a method and a system for monitoring a posture of the present invention will be described in detail with reference to FIGS. 3 and 4.

Figure 3:
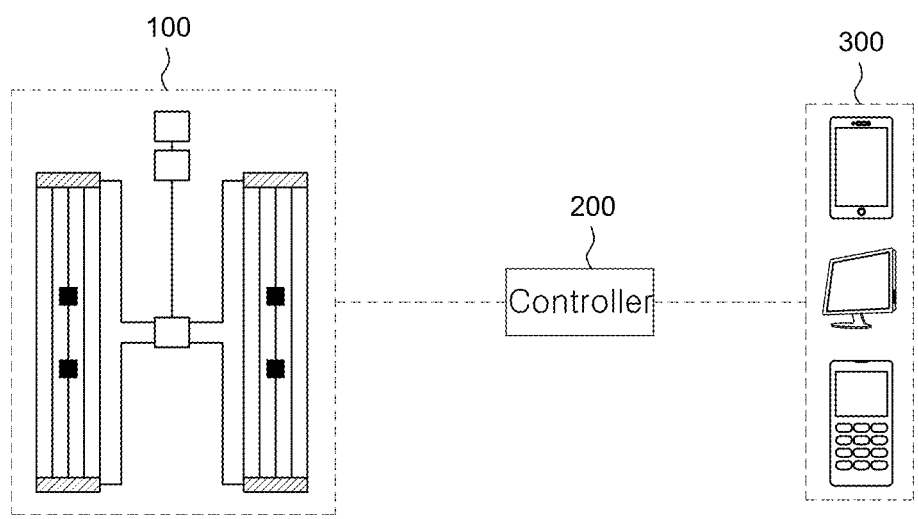
FIG. 3 is a block diagram schematically illustrating a posture monitoring system according to an exemplary embodiment of the present invention.
Figure 4:
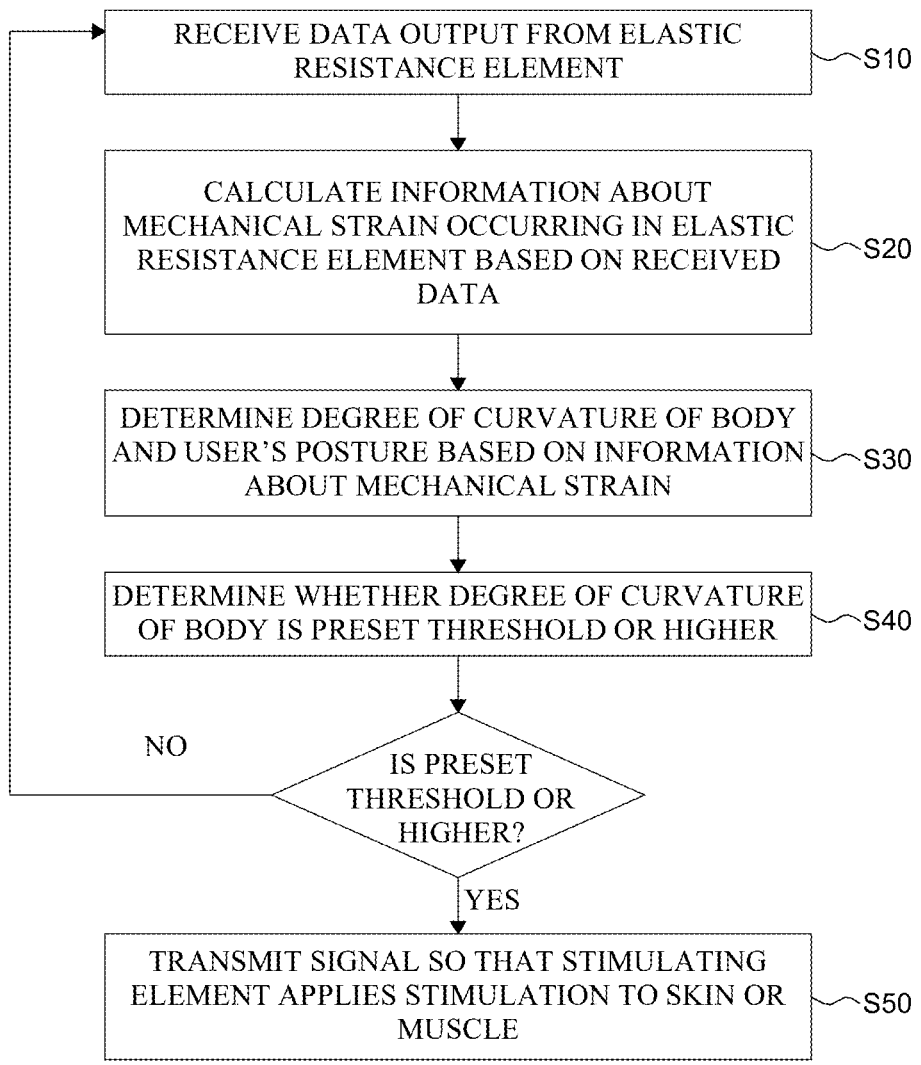
FIG. 4 is a flowchart for describing a posture monitoring method according to an exemplary embodiment of the present invention.

FIG. 3 is a block diagram schematically illustrating a posture monitoring system according to an exemplary embodiment of the present invention and FIG. 4 is a flowchart for describing a posture monitoring method according to an exemplary embodiment of the present invention.

Referring to FIG. 3, a posture monitoring system of the present invention includes a posture monitoring device 100, a controller 200, and a user terminal 300. The posture monitoring device 100 is as described above with reference to FIGS. 1, 2A and 2B.

The controller 200 processes various data for performing the posture monitoring method of the present invention.

Specifically, the controller 200 receives data output from the first elastic resistance element 110 and the second elastic resistance element 120 of the posture monitoring device 100 to determine the degree of stretching of the first part 11 and the second part 12 on a dorsal part and determine the degree of curvature of the body and the posture based on the determined degree of stretching. In addition, when the determined degree of curvature of the body is greater than or equal to a preset threshold, the controller 200 may provide a stimulation signal to the first stimulating element 160 and the second stimulating element 170 to correct the user's posture.

The controller 200 may correspond to at least one processor or may include at least one processor.

In addition, the controller 200 may be implemented as a separate device and driven as illustrated in the drawing, or may be driven in a form included in another hardware device (e.g., the user terminal 300) such as a microprocessor or a general purpose computer system. Hereinafter, the controller 200 may be implemented as a separate device to perform the posture monitoring method of the present invention, but the present invention is not limited thereto.

The user terminal 300 may be a communication terminal capable of using a web or mobile service in a wired or wireless communication environment. Specifically, the user terminal 300 may be a device or a terminal including a processor, a storage unit, a communication module, and may be a general purpose computer, a special purpose computer, a mobile terminal such as a smart phone, a desktop or laptop computer, or an accessory device used in combination with them. The user terminal 300 may include a display unit that displays a screen and an input device that receives data from a user.

The user terminal 300 may communicate with the controller 200 and share posture information of the user measured by the posture monitoring device 100, and may also transmit a signal input to the user terminal 300 to the posture monitoring device 100 through the controller 200.

Hereinafter, for convenience of description, it is assumed that the user terminal 300 is a smart phone equipped with an application related to the posture monitoring method of the present invention, but the present invention is not limited thereto, and of course, the user terminal 300 may be one of the terminals listed above.

Hereinafter, a method of performing the posture monitoring method of the present invention by the controller 200 will be described with reference to FIG. 4. For understanding of the invention, the drawings illustrated in FIGS. 1 to 3 may be referred together.

The controller 200 receives data output from the first elastic resistance element 110 and the second elastic resistance element 120 from the communication module 150 of the posture monitoring device 100 (S10).

Here, the data is data relating to the current, voltage, and resistance of the first elastic resistance element 110 and the second elastic resistance element 120.

The controller 200 calculates information on mechanical strain generated in the first elastic resistance element 110 and the second elastic resistance element 120 based on the received data (S20), and determines the user's posture by measuring the degree of curvature of the body in the first part and the second part based on the calculated information on mechanical strain (S30).

A principle is as follows in which the controller 200 calculates the information on mechanical strain generated in the first elastic resistance element 110 and the second elastic resistance element 120 through the data output from the first elastic resistance element 110 and the second elastic resistance element 120 and determines the user's posture by measuring the degree of stretching of the first part 11 and the second part 12 of the dorsal part and the degree of curvature of the body.

When the first part 11 and the second part 12 of the dorsal part are stretched, the lengths of the first elastic resistance element 110 and the second elastic resistance element 120 are increased, but the thicknesses of the first elastic resistance element 110 and the second elastic resistance element 120 are decreased. At this time, the resistances of the first elastic resistance element 110 and the second elastic resistance element 120 are increased. On the contrary, when the first part 11 and the second part 12 of the dorsal part are contracted, the lengths of the first elastic resistance element 110 and the second elastic resistance element 120 are decreased, but the thicknesses of the first elastic resistance element 110 and the second elastic resistance element 120 are increased. At this time, the resistances of the first elastic resistance element 110 and the second elastic resistance element 120 are decreased.

In this principle, the controller 200 calculates changes in resistances of the first elastic resistance element 110 and the second elastic resistance element 120 to measure the degree of stretching of the first part 11 and the second part 12 of the dorsal part in which the first elastic resistance element 110 and the second elastic resistance element 120 are disposed.

For example, if the resistance of the first elastic resistance element 110 is increased and the resistance of the second elastic resistance element 120 is increased, both the first part 11 and the second part 12 of the dorsal part are stretched, and thus, the controller 200 determines the user's posture as a posture of bending the back or waist or lowering the head.

On the contrary, if the resistance of the first elastic resistance element 110 is decreased and the resistance of the second elastic resistance element 120 is decreased, both the first part 11 and the second part 12 of the dorsal part are contracted, and thus, the controller 200 determines the user's posture as a posture of bending back the back or waist or raising the head.

Meanwhile, if the resistance of the first elastic resistance element 110 is decreased and the resistance of the second elastic resistance element 120 is increased, or the resistance of the first elastic resistance element 110 is increased and the resistance of the second elastic resistance element 120 is decreased, one of the first part 11 and the second part 12 of the dorsal part is stretched and the other part is contracted, and thus, the controller 200 determines the user's posture as being inclined to the left or right or rotating the trunk.

Next, the controller 200 determines whether the degree of curvature of the body in the first part 11 and the second part 12 is equal to or greater than a preset threshold (S40).

When the degree of curvature of the body is equal to or greater than the preset threshold, it means that the user takes an incorrect posture, that is, an improper posture at the time of measuring.

Here, the preset threshold may be appropriately set for the user who uses the posture monitoring device 100 of the present invention and preset in the controller 200.

For example, while the user naturally sits or stands (standing position), a setting point is set, and the degree of curvature of the body is measured by setting intentionally each part of the body by flexion, extension, lateral rotation, and lateral bending. In this case, a technique such as radiographic imaging may be utilized. Between the standing position of the user and the position where the body is strained to the maximum value, the degree of deviating from the standing position at a predetermined ratio may be determined as the preset threshold.

At this time, the controller 200 may record a time that the degree of curvature of the body lasts at the preset threshold or higher to make a database for giving feedback to the user, and transmit the recorded time to the user terminal 300 to make it for the user to check the monitoring content for the own posture.

Next, when the controller 200 determines whether the degree of curvature of the user's body is equal to or greater than the preset threshold, the controller 200 transmits a signal so that at least one of the first stimulating element 160 and the second stimulating element 170 applies stimulation to the skin or muscle (S50).

For example, on the other hand, when the controller 200 determines that the second part 12 of the dorsal part is stretched by the preset threshold or higher by decreasing the resistance of the first elastic resistance element 110 and increasing the resistance of the second elastic resistance element 120, the controller 200 may transmit a signal to the second stimulating element 170 to apply stimulation to the skin or muscle.

Through this feedback process, the muscle on the side applied with the stimulation may be contracted, and at the same time, the user may sense the stimulation to correct the posture.

On the other hand, when the controller 200 determines whether the degree of curvature of the user's body is equal to or greater than the preset threshold, the controller 200 may transmit an alarm signal to the user terminal 300. When the alarm signal is transmitted to the user terminal 300 as sound, vibration, or visual information, the user may also sense the stimulation to correct the posture.

According to the posture monitoring device, method, and system of the present invention, when the user maintains an improper posture for a predetermined time or higher, a signal to correct the posture is transmitted to the user, thereby preventing diseases such as discopathy (disc disease) of the spinal column or cyphosis and scoliosis caused by the improper posture. Further, by inducing patients having surgery due to a spinal lesion and required to maintain a correct posture for a certain period of time to maintain the correct posture, it is possible to prevent postoperative complications.

Hereinabove, the exemplary embodiments of the present invention have been described with the accompanying drawings, but it can be understood by those skilled in the art that the present invention can be executed in other detailed forms without changing the technical spirit or requisite features of the present invention. Therefore, it should be appreciated that the aforementioned exemplary embodiments described above are all illustrative in all aspects and are not restricted.

What is claimed:

1. A posture monitoring device configured to monitor a posture by measuring a degree of stretching of a first part and a second part of a dorsal part which are divided by a spinal column, the posture monitoring device comprising:
   at least one first elastic resistance element which includes a pair of first electrodes respectively formed on opposite ends of each of the at least one first elastic resistance element, and a first conductive material that has elasticity and is connected to each of the pair of first electrodes, the at least one first elastic resistance element disposed in a longitudinal direction of the spinal column and configured to be attached onto or inserted into skin of the first part, the first conductive material configured to be formed as a string through a combination of elastic materials and conductive nanoparticles, and to exhibit electrical resistance that changes according to a mechanical strain occurring in the at least one first elastic resistance element;
   at least one second elastic resistance element which includes a pair of second electrodes respectively formed on opposite ends of each of the at least one second elastic resistance element, and a second conductive material that has elasticity and is connected to each of the pair of second electrodes, the at least one second elastic resistance element disposed in the longitudinal direction of the spinal column and configured to be attached onto or inserted into skin of the second part, the second conductive material configured to be formed as a string through a combination of elastic materials and conductive nanoparticles, and to exhibit electrical resistance that changes according to a mechanical strain occurring in the at least one second elastic resistance element;
   a power supply configured to apply a current or a voltage to the at least one first elastic resistance element and the at least one second elastic resistance element through the electrodes formed on both ends of each of the at least one first elastic resistance element and the at least one second elastic resistance element; and
   a meter configured to be connected to each electrode of the pair of first electrodes and the pair of second electrodes in order to measure current or voltage flowing in the at least one first elastic resistance element and current or voltage flowing in the at least one second elastic resistance element.

2. The posture monitoring device of claim 1,
   wherein the at least one first elastic resistance element includes a plurality of first elastic resistance elements, and
   wherein the at least one second elastic resistance element includes a plurality of second elastic resistance elements.

3. The posture monitoring device of claim 1, further comprising:
   a first stimulating electrode configured to be attached onto or inserted into the skin of the first part and to apply stimulation to the skin or muscle of the first part; and
   a second stimulating electrode configured to be attached onto or inserted into the skin of the second part and to apply stimulation to the skin or muscle of the second part.

4. The posture monitoring device of claim 1, further comprising:
   a third elastic resistance element which includes a pair of third electrodes respectively formed on opposite ends of the third elastic resistance element, and a third conductive material that has elasticity and is connected to each of the pair of third electrodes, the third elastic resistance element disposed in a direction perpendicular to the longitudinal direction of the spinal column and configured to be attached onto or inserted into skin of a third part of the dorsal part,
   wherein the third conductive material is configured to be formed as a string through a combination of elastic materials and conductive nanoparticles, and to exhibit electrical resistance that changes according to a mechanical strain occurring in the third elastic resistance element.

5. The posture monitoring device of claim 4, further comprising:
   a stimulating electrode configured to be attached onto or inserted into the skin of the third part and to apply stimulation to the skin or muscle of the third part.

6. The posture monitoring device of claim 1, further comprising:
a third elastic resistance element which includes a pair of third electrodes respectively formed on opposite ends of the third elastic resistance element, and a third conductive material that has elasticity and is connected to each of the pair of third electrodes, the third elastic resistance element disposed in a direction parallel to the longitudinal direction of the spinal column and configured to be attached onto or inserted into skin of a third part of the dorsal part,
wherein the third conductive material is configured to be formed as a string through a combination of elastic materials and conductive nanoparticles, and to exhibit electrical resistance that changes according to a mechanical strain occurring in the third elastic resistance element.

7. The posture monitoring device of claim 6, further comprising:
a stimulating electrode configured to be attached onto or inserted into the skin of the third part and to apply stimulation to the skin or muscle of the third part.

8. A posture monitoring method configured to monitor a posture by measuring a degree of stretching of a first part and a second part of a dorsal part which are divided by a spinal column, the posture monitoring method comprising:
receiving data of at least one of current and voltage output from a first elastic resistance element and a second elastic resistance element, from a posture monitoring device including
the first elastic resistance element which includes a pair of first electrodes respectively formed on opposite ends of the first elastic resistance element, and a first conductive material that has elasticity and is connected to each of the pair of first electrodes, the first elastic resistance element disposed in a longitudinal direction of the spinal column and configured to be attached onto or inserted into skin of the first part, the first conductive material configured to be formed as a string through a combination of elastic materials and conductive nanoparticles, and to exhibit electrical resistance that changes according to a mechanical strain occurring in the first elastic resistance element,
the second elastic resistance element which includes a pair of second electrodes respectively formed on opposite ends of the second elastic resistance element, and a second conductive material that has elasticity and is connected to each of the pair of second electrodes, the second elastic resistance element disposed in the longitudinal direction of the spinal column and configured to be attached onto or inserted into skin of the second part, the second conductive material configured to be formed as a string through a combination of elastic materials and conductive nanoparticles, and to exhibit electrical resistance that changes according to a mechanical strain occurring in the second elastic resistance element, and
a power supply configured to apply a current or a voltage to the first elastic resistance element and the second elastic resistance element through the electrodes formed on both ends of each of the first elastic resistance element and the second elastic resistance element,
wherein the electrical resistance that changes according to the mechanical strain occurring in the first elastic resistance element is determined based on the current or voltage flowing in the first elastic resistance element, and
wherein the electrical resistance that changes according to the mechanical strain occurring in the first elastic resistance element is determined based on the current or voltage flowing in the second elastic resistance element;
calculating information about the mechanical strains respectively occurring in the first elastic resistance element and the second elastic resistance element, based on the data; and
measuring a degree of curvature in each of the first part and the second part based on the information about the mechanical strains.

9. The posture monitoring method of claim 8, further comprising:
determining whether the degree of curvature in either of the first part or the second part is at or above a present threshold.

10. The posture monitoring method of claim 9,
wherein the posture monitoring device further includes
a first stimulating electrode configured to be attached onto or inserted into the skin of the first part and to apply stimulation to the skin or muscle of the first part and
a second stimulating electrode configured to be attached onto or inserted into the skin of the first part and to apply stimulation to the skin or muscle of the second part, and
wherein the method further comprises:
transmitting, from the posture monitoring device, a signal so that at least one of the first stimulating element and the second stimulating element applies stimulation to the skin or muscle, when the degree of curvature in at least one of the first part and the second part is determined as being at or above the preset threshold and is maintained for a predetermined time or longer.

11. The posture monitoring method of claim 9, further comprising:
transmitting, from the posture monitoring device, an alarm signal to an external terminal, when the degree of curvature in at least one of the first part and the second part is determined as being at or above the preset threshold and is maintained for a predetermined time or longer.

12. A posture monitoring system configured to monitor a posture by measuring a degree of stretching of a first part and a second part of a dorsal part which are divided by a spinal column, the posture monitoring system comprising:
a posture monitoring device including:
a first elastic resistance element which includes a pair of first electrodes respectively formed on opposite ends of the first elastic resistance element, and a first conductive material that has elasticity and is connected to each of the pair of first electrodes, the first elastic resistance element disposed in a longitudinal direction of the spinal column and configured to be attached onto or inserted into skin of the first part, the first conductive material configured to be formed as a string through a combination of elastic materials and conductive nanoparticles, and to exhibit electrical resistance that changes according to a mechanical strain occurring in the first elastic resistance element,
a second elastic resistance element which includes a pair of second electrodes respectively formed on opposite ends of the second elastic resistance element, and a second conductive material that has elasticity and is connected to each of the pair of second electrodes, the second elastic resistance element disposed in the longitudinal direction of the spinal column and configured to be attached onto or inserted into skin of the second part, the second conductive material configured to be formed as a string through a combination of elastic materials and conductive nanoparticles, and to exhibit electrical resistance that changes according to a mechanical strain occurring in the second elastic resistance element, a power supply configured to apply a current or a voltage to the first elastic resistance element and the second elastic resistance element through the electrodes formed on both ends of each of the first elastic resistance element and the second elastic resistance element, and a meter configured to be connected to each electrode of the pair of first electrodes and the pair of second electrodes in order to measure current or voltage flowing in the first elastic resistance element and current or voltage flowing in the second elastic resistance and element, the posture monitoring system further comprising a controller configured to:

receive data of at least one of current and voltage output from the first elastic resistance element and the second elastic resistance element, from the posture monitoring device, calculate information about the mechanical strains respectively occurring in the first elastic resistance element and the second elastic resistance element, based on the data, and measure a degree of curvature in each of the first part and the second part based on the information about the mechanical strains.

* * * * *